(12) United States Patent
Karageozian

(10) Patent No.: US 6,737,075 B2
(45) Date of Patent: May 18, 2004

(54) BIOCHEMICAL METHODS THAT ELIMINATE CORNEAL SCARS, OPACIFICATION AND HAZE

(75) Inventor: Hampar Karageozian, San Juan Capistrano, CA (US)

(73) Assignee: Ista Pharmaceuticals, Inc., Irvine, CA (US)

( * ) Notice: Subject to any disclaimer, the term of this patent is extended or adjusted under 35 U.S.C. 154(b) by 2 days.

(21) Appl. No.: 09/975,039

(22) Filed: Oct. 10, 2001

(65) Prior Publication Data

US 2002/0119141 A1 Aug. 29, 2002

Related U.S. Application Data

(63) Continuation of application No. PCT/US00/11369, filed on Apr. 28, 2000.
(60) Provisional application No. 60/131,558, filed on Apr. 29, 1999.

(51) Int. Cl.$^7$ .......................... A61F 2/14; A61K 13/02; A61K 31/74; A61K 38/46; A61K 38/48
(52) U.S. Cl. .................... 424/427; 424/434; 424/78.04; 424/94.62; 424/94.63; 424/94.64
(58) Field of Search .................... 424/423, 427, 424/434, 78.04, 94.62, 94.63, 94.64

(56) References Cited

U.S. PATENT DOCUMENTS

| | | | |
|---|---|---|---|
| 4,174,389 A | | 11/1979 | Cope |
| 5,626,865 A | * | 5/1997 | Harris et al. ................. 424/427 |
| 5,788,957 A | | 8/1998 | Harris |
| 6,039,943 A | * | 3/2000 | Karageozian et al. ..... 424/94.62 |

FOREIGN PATENT DOCUMENTS

| | | |
|---|---|---|
| EP | 0 567 816 A1 | 11/1993 |
| WO | 98/52602 | 11/1998 |

OTHER PUBLICATIONS

Angelo, S.J. (1971) Therapy and management of some ocular diseases in the bovine. The Indian Veterinary Journal. 48:310–315.

Kiyoo, et al. (1996) Glycosaminoglycans in subepithelial opacity after excimer laser keratectomy. Biosciences Information Service, Philadelphia, PA. Database accession No. PREV199699096049 XP002153662 abstract.

Magrane, W.G. (1971) Canine Opthalomology. Lea & Febiger, Philadelphia. 5 pages.

Misra, et al. (1982) Note on the clinical efficacy of subconjunctival hyaluronidase in corneal opacity in animals. Indian Journal of Animal Sciences. 52(5):360–361.

Yee et al. (1994) Treatment with streptokinase in experimental penetrating keratoplasty in rabbits. Investigative Ophthalmology & Visual Science. 35(4):1878.

Philip B. Hawk, Hawk's Physiological Chemistry (Bernard L. Oeer, Ph.D. ed., Mcgraw–Hill, 14$^{th}$ ed. 1965).

* cited by examiner

*Primary Examiner*—Carlos A. Azpuru
(74) *Attorney, Agent, or Firm*—Knobbe, Martens, Olson & Bear LLP

(57) ABSTRACT

The invention disclosed herein relates to biochemical methods for the elimination of corneal collagen fiber disorganization to improve vision. Disorganization of corneal collagen fibers is seen in corneal scars, corneal opacification and corneal haze. In addition, the invention relates to biochemical methods for the elimination of corneal collagen fiber disorganization resulting from accidental traumatic injury to the cornea and from refractive surgery for such as radial keratotomy (RK), photorefractive keratectomy (PRK), and laser in situ keratomileusis (LASIK) so as to improve visual acuity and quality of vision.

15 Claims, No Drawings

BIOCHEMICAL METHODS THAT ELIMINATE CORNEAL SCARS, OPACIFICATION AND HAZE

CROSS REFERENCE TO RELATED APPLICATIONS

This application claims the benefit of priority from PCT/US00/11369, filed Apr. 28, 2000, and published in English under PCT Article 21(2), which claims the benefit of priority from U.S. Provisional Application No. 60/131,558, filed Apr. 29, 1999, each of which is hereby incorporated by reference in their entirety.

FIELD OF THE INVENTION

The invention disclosed herein relates to biochemical methods for the elimination of corneal scars, opacification and haze.

BACKGROUND OF THE INVENTION

The cornea is the transparent dome on the front of the eye through which light passes. About eighty percent of the focus, or refracting, power of the eye is in the cornea. A reduction of visual acuity and blindness may result from a lack of corneal clarity caused by corneal traumas, corneal scars, or any other cause of corneal opacification.

The global prevalence of eyes with severe corneal opacities is estimated at more than three million, with over 200,000 new cases being added to this pool every year. The current treatment for corneal opacity associated with significant visual impairment is a form of corneal transplantation, called penetrating or lamellar keratoplasty (PKP, LKP), using tissue from corneal donors. While this surgical technique is generally regarded as safe and effective, associated risks include graft failure or rejection, and infections transmitted through the donor cornea (e.g., rabies, HIV, etc.) or the surgical procedure (e.g., HIV, staph infections, etc.) Notwithstanding the various side-effects, the number of corneal transplant surgeries that can be performed is limited by the number of corneas available for transplantation. To date, the availability of donor corneal tissue suitable for transplant has failed to meet the needs of the patient population.

Present methods of correcting refractive errors of the eye, such as eye glasses, contact lenses, radial keratotomy, photorefractive keratotomy or laser in-situ keratomileusis are not useful in the elimination of corneal opacification. Preliminary evidence suggests that radial keratotomy, photorefractive keratotomy, and laser in-situ keratomileusis may cause corneal haze in some patients.

What is needed to treat the loss of corneal transparency is a biochemical, non-surgical method of treatment that produces a cornea with increase transparency. The methods and compositions taught herein satisfy this long-felt need.

SUMMARY OF THE INVENTION

The invention disclosed herein relates to biochemical methods for the elimination of corneal collagen fiber disorganization to improve vision. Disorganization of corneal collagen fibers is seen in corneal scars, corneal opacification and corneal haze. In addition, the invention relates to biochemical methods for the elimination of corneal collagen fiber disorganization resulting from accidental traumatic injury to the cornea or from refractive surgery for such as radial keratotomy (RK), photorefractive keratectomy (PRK), and laser in situ keratomileusis (LASIK) so as to improve visual acuity and quality of vision.

DETAILED OF DESCRIPTION OF THE INVENTION

The invention disclosed herein relates to improving corneal clarity using non-surgical, biochemical compositions and methods. The biochemical methods for eliminating corneal scars, corneal opacification, and optical aberrations including corneal haze in the eye of a subject mammal without corneal surgery are achieved by treating the source of the corneal distortion. The compositions and methods of the disclosed invention relate to reducing corneal collagen disorganization by biochemical modification of corneal stromal glycoproteins and proteoglycans.

The cornea is a transparent, multi-component structure of the eye through which light passes to reach the retina. The transparency of the cornea to light results from the unique extracellular matrix of the corneal stroma. The stroma is a tissue layer organized into collagenous lamellae of tightly packed parallel collagen fibers embedded in a hydrated matrix of glycoproteins and proteoglycans. The size, regularity, and precise spacing of the fibrillar structures are the physical characteristics essential for corneal transparency (Maurice, 1957).

The role of corneal glycoproteins and proteoglycans in the establishment and maintenance of corneal transparency is not well understood. Stromal proteoglycans have been hypothesized to play a role in the regulation of collagen fiber spacing. (Hassell et al., 1983). Although the precise role of proteoglycans is still unclear, they are thought to influence the hydration, thickness and clarity of the cornea. (Borcheding et al., 1975). The functional significance of hyaluronan in the cornea, except during development (Toole and Trelstad, 1971) and in some corneal abnormalities (Fitzsimmons et al., 1994) is still unknown.

In some opaque human corneal scars, the scars have been found to contain collagen fibrils with abnormally large diameter and irregular interfibrillar spacing. (Schwarz and Keyserlingk, 1969). However, during wound healing of rabbit corneas, the early opaque scars contain collagen fibrils of generally normal diameter that are irregularly spaced within the tissue. The collagen fibril diameter does not markedly change after a year of healing, but the spacing between the fibrils returns to normal and there is a concomitant decrease in the opacity of the scar. (Cintron & Kublin, 1977 and Cintron et al., 1978).

A 1983 paper authored by Hassell et al., showed that opaque scars that contained large interfibrillar spaces also contained unusually large chondroitin sulfate proteoglycans with glycosaminoglycan side chains of normal size. These opaque scars also lacked the keratan sulfate proteoglycan but did contain hyaluronic acid. The biochemical analysis of proteoglycans in rabbit corneal scars in corneal wounds compared to normal cornea adjacent to the scar demonstrates that the areas synthesize proteoglycans measurably different from one another. (Cintron et al., 1990).

Hassell et al. (1980) analyzed corneal specimens obtained during surgery from patients with macular corneal dystrophy. Hassell et al. found that cells from normal corneas synthesized both a chondroitin sulfate proteoglycan and a keratan sulfate proteoglycan similar to those present in monkey and bovine corneas. Cells in macular corneal dystrophy synthesized a normal chondroitin sulfate proteoglycan, but did not synthesize either keratan sulfate or a mature keratan sulfate proteoglycan. Instead, the cells synthesized a glycoprotein with an unusually large oligosaccharide side chain.

As discussed above, various traumas to the cornea result in the formation of corneal scars or opacification. The opacity of the scar tissue itself results from corneal collagen fibers that have grown during the healing process and lack the same level of organization found in undamaged corneal tissue. Penetrating keratoplasty, which uses corneal tissue from donor corneas in the form of corneal graft is the only surgical technique presently available to eliminate corneal scars or opacification. The challenges associated with penetrating keratoplasty are: (a) availability of human donor corneas for surgery; (b) compatibility of donor corneas and probability of graft survival; (c) donor cornea graft rejection; (d) donor cornea infection. The compositions and methods of the disclosed invention offer a non-surgical alternative to penetrating keratoplasty.

The transparency of the cornea may be altered in a manner more subtle than that seen in the corneal traumas described above. In certain situations the appearance of optical, monochromatic aberrations may decrease the visual acuity (VA) of a subject's eye. On the basis of the mosaic structures of the retina, the visual acuity of the human eye could be 20/10 or better; however, such good acuity is rarely obtained. Two optical conditions accounting for the sub-optimal level of visual acuity are: diffraction due to pupil size and monochromatic aberrations. (Campbell, et al., 1974). The limitations of visual acuity caused by diffraction decreases with increasing pupil diameter and may play an important role only for pupils smaller than 2 mm. The optical errors of higher order (aberrations) of the human eye, however, demonstrates an opposite behavior and may increase with larger pupil diameter.

The shape of the human cornea and lens is naturally designed in a way that these aberrations are minimized. To our knowledge, the monochromatic aberrations of the human eye so far have not been studied systematically in large series of individuals. (Howland, et al., 1977). Therefore, average values for a standard population are not available. However, loss of visual acuity through the introduction of optical aberrations may become clinically relevant with the advent of refractive corrective surgery.

Refractive surgery for myopia and astigmatism, such as radial keratotomy (RK), photorefractive keratectomy (PRK), and laser in situ keratomileusis (LASIK), induce a non-physiological corneal shape with a flat central area and increasing power towards the periphery. This shape induces an increase in optical aberrations (Seiler T et al., 1993), (Pallikaris I., 1998), and may lead to visual losses that are detected under low lighting conditions (Seiler T, et al., 1994), and by low contrast visual acuity testing (Verdon W., 1996). These side effects of corneal refractive surgery have the potential for public health problems of a yet unknown dimension.

Comparison of corneal wavefront aberrations after PRK and LASIK has been compared in a prospective randomized study of 22 patients with bilateral myopia who received PRK on one eye and LASIK in the other eye. (Oshika T et al., 1999). Before surgery, simulated papillary dilation from 3 mm to 7 mm caused a five to six fold increase in the total aberrations. After surgery, the same dilation resulted in a 25 to 32 fold increase in the total aberrations in the PRK group and a 28 to 46 fold increase in total aberrations in the LASIK. Both photorefractive keratectomy and laser in situ keratomileusis significantly increased the total wavefront aberrations and the values did not return to the preoperative level throughout the 12-month follow-up period.

Corneal wound healing studies in rabbits following LASIK to evaluate the corneal wound healing process were conducted for 1, 2 and 9 months past LASIK surgery. Periodic histopathological evaluation of the rabbit corneas showed disorganized collagen fibers along the interface of the corneal flap even 9 months after the LASIK surgery. These results show that the corneal aberrations and the wound healing process induced by the LASIK surgery continued at 9 months after LASIK. (Kato T, 1999). The methods and compositions of the invention disclosed herein provide the means with which to overcome the optical aberration side-effect of modem refractive surgical techniques.

Without being restricted to any particular mechanism of action, it has been theorized that the various corneal aberrations resulting from RK, PRK, LASIK, and other surgical procedures result from corneal collagen disorganization that occurs during the healing process. For example, following the LASIK procedure, after the flap is positioned to cover the site of the surgical procedure, corneal collagen will be formed to seal the incision. As this collagen is formed it is thought to be arranged in a conformation that is, to one degree or another, less organized than the collagen located in areas of the cornea not affected by the surgery. Reorganization of this material would lead to a reduction in optical aberrations resulting from such surgeries.

Accordingly, the disclosed invention relates to a biochemical method for the elimination of corneal aberrations and corneal collagen fiber disorganization resulting from accidental traumatic injury to the cornea or from refractive surgery for myopia, hyperopia and astigmatism, such as radial keratotomy (RK), photorefractive keratectomy (PRK), and laser in situ keratomileusis (LASIK) so as to improve visual acuity and quality of vision.

Corneal Collagen Reorganizing Enzymes and Agents

The disclosed invention provides for the introduction of particular compositions into a subject's cornea to improve the visual acuity of the subject. The compositions contemplated for use include a number of enzymes or other agents that result in the reorganization of corneal collagen fibers. Of particular interest are enzymes that act to alter, digest, or otherwise degrade various components that decorate or are in association with the corneal collagen fibers. However, the methods and compositions of the disclosed invention are not limited to the use of these enzymes and agents, and include other chemicals that can be administered to reorganize corneal collagen fibers through various different mechanisms of action.

One embodiment of the disclosed invention provides for the administration of a corneal collagen fiber reorganizing amount of an enzymes which, when contacted with the corneal stroma, will accelerate the rate of breakdown of corneal proteoglycans and lead to the reorganization of corneal collagen. The resulting reorganization will clear corneal scars, corneal opacities and corneal haze.

A variety of glycoaminoglycanase enzymes are contemplated for use with the disclosed invention. These enzymes all exhibit the property of providing a corneal opacity clearing effect as well as the ability to eliminate corneal aberrations and corneal collagen fiber disorganization. Specific enzymes include: hyaluronidase, keratinase, chondroitinase AC, chondroitinase B, chondroitinase ABC, and chondroitin 4 sulfatase.

A variety of metalloproteinase enzymes are contemplated for use with the disclosed invention. These metalloproteinase enzymes exhibit a corneal opacity clearing effect and have the ability to eliminate corneal aberrations and corneal collagen fiber disorganization. Specific examples of suitable enzymes include: matrix metalloproteinase-1, matrix metalloproteinase-2, matrix metalloproteinase-3, and matrix metalloproteinase-9.

Various protein-kinase enzymes that exhibit a corneal opacity clearing effect as well as the ability to eliminate corneal aberrations and corneal collagen fiber disorganization are also contemplated for use with the disclosed invention. Specific examples of such enzymes include: streptokinase and urokinase.

In addition to these enzymes, other enzymes known in the art that alter and modify corneal collagen fibrillar structure may be used with the methods of the disclosed invention. Suitable enzymes induce modifications to corneal collagen or the components thereof that decrease corneal opacification and corneal optical aberrations.

Formulations

The invention disclosed here contemplates a number of different formulations that are effective in producing the reorganization of corneal collagen. One embodiment of the invention contemplates the formulation of an injectable solution containing a corneal collagen reorganizing enzyme. The injectable solution may contain certain inactive ingredients which cause the solution to be substantially isotonic and of a pH which is suitable for injection into the eye. Such solution for injection may be initially lyophilized to a dry state and thereafter, may be reconstituted prior to use.

A general formulation for an injectable thimerosal-free, hyaluronidase preparation, of the present invention is shown in Table I as follows:

TABLE I

General Formulation

| Ingredient | Quantity |
| --- | --- |
| Hyaluronidase/Hyaluronidase (ACS) | up to 8000 IU |
| Lactose, USP/sorbitol | 13.3 mg–130.0 mg |
| Phosphate, USP | 5–200 mmoles |

This formulation of ingredients is produced by initially dissolving the ingredients in sterile water, sterile filtering the solution and subsequently dispensed as a solution or lyophilized to a dry composition. The lyophilized composition can be packaged for subsequent reconstitution prior to use, in balanced salt solution or sterile isotonic saline solution. Such balanced salt solution typically contains: 0.64% sodium chloride, 0.075% potassium chloride, 0.048% calcium chloride dihydrate, 0.03% sodium acetate trihydrate, 0.17% sodium citrate dihydrate, sodium hydroxide/hydrochloric acid to adjust the pH, and water for injection to 100%.

Many kinds of hyaluronidase enzyme free of thimerosal preservative could be used, however, the term "hyaluronidase ACS" as used herein describes a preferred hyaluronidase, which is devoid of hyaluronidase molecular weight fractions above 100,000, between 60,000–70,000 and below 40,000 (10% SDS-PAGE). Such hyaluronidase may be derived from ovine testicles and is available on request from Biozyme Biochemicals, 9939 Hilbert Street, San Diego, Calif. 92131-1029. Applicants have determined that this specific molecular weight distribution of the hyaluronidase ACS results in less ophthalmic toxicity than other hyaluronidase preparations, while exhibiting desirable therapeutic efficacy in a number of ophthalmic applications.

The specific molecular weight distribution and specific enzyme activity profile of the preferred hyaluronidase (ACS) of the present invention, and/or the exclusion of thimerosal from its formulation, provides a hyaluronidase preparation which is non-toxic to the eye when administered at dosage levels at which other hyaluronidase preparations preserved with thimerosal would cause toxic effects.

TABLE II

Specific Formulation

| Ingredient | Quantity |
| --- | --- |
| Hyaluronidase/Hyaluronidase (ACS) | 1 IU–8000 IU |
| Lactose USP/Sorbitol | 13.3 mg–150 mg |
| Phosphate USP | 5 mmoles–50 mmoles |
| Sodium Chloride USP | Make isotonic |

TABLE III

Specific Formulation

| Ingredient | Quantity |
| --- | --- |
| Hyaluronidase/Hyaluronidase (ACS) | 1 IU–50,000 IU |
| Lactose USP/Sorbitol | 13.3 mg–150 mg |
| Phosphate USP | 5 mmoles–50 mmoles |
| Sodium Chloride USP | Make isotonic |
| Sterile water for Injection USP | QS to 2.0 mL |

(Hyaluronidase concentration 500 IU/20 μl)

TABLE IV

Specific Formulation

| Ingredient | Quantity |
| --- | --- |
| Hyaluronidase/Hyaluronidase (ACS) | 2500 IU |
| Lactose USP/Sorbitol | 10 mg |
| Phosphate USP | 5 mmoles |
| Sodium Chloride USP | Make isotonic |
| Sterile water for Injection | QS to 2.0 mL |

(Hyaluronidase concentration 25 IU/20 μl)

TABLE V

Specific Formulation

| Ingredient | Quantity |
| --- | --- |
| Hyaluronidase/Hyaluronidase (ACS) | 100 IU |
| Lactose USP/Sorbitol | 10 mg |
| Phosphate USP | 5 mmoles |
| Sodium Chloride USP | Make isotonic |
| Sterile water for Injection | QS to 2.0 mL |

(Hyaluronidase concentration 1 IU/20 μl)

As described in the examples below, the specific preferred formulation as hyaluronidase ACS set forth in Tables II–V (above) may be injected, applied topically, or by contact lens directly into the stroma of the eye at dosage levels which bring about desirable therapeutic effects, including but not necessarily limited to the elimination of a corneal opacity, without causing significant toxicity to the eye.

Determining Suitable Corneal Collagen Reorganizing Enzymes and Agents and their Dosages The corneal collagen reorganizing chemicals, such as various agents and enzymes, used in the methods of the disclosed invention, in addition to the proper dosages of such agents and enzymes, can be determined by one of skill in the art through routine experimentation. Such experimentation can comprise testing a dose of an enzyme or agent on donor globes (eyes) mounted in plastic model sockets or testing such a dose on laboratory animals. Briefly, to determine whether an enzyme or agent is effective in reorganizing the collagen of a cornea without producing toxicity, the enzyme or agent is first mixed in a carrier vehicle that is pharmaceutically acceptable to a mammal. Preferably, the enzyme or agent is in lyophilized (dry powder) form, and is dissolved in isotonic saline. However, one of ordinary skill in the art will understand that a variety of pharmacologically acceptable carriers which do not interfere with the functioning of an enzyme or agent can be used. Such a procedure is also followed to test various doses of a compound of interest.

A test dose of the enzyme or agent in solution is then administered to a test cornea in order to determine its corneal collagen reorganizing and toxic effects. In one procedure for testing candidates, the test enzyme or agent is first administered to corneas. This procedure is particularly preferred for determining the effect of an enzyme or agent on a human cornea because in this way a human cornea can be tested without subjecting a living person to experimentation.

The test dose of enzyme or agent is then administered to the donor cornea. Such administration can be, for example, by injection of the enzyme into the cornea. Normally, the lens will become opacified following this step due to the introduction of water into the eye and a change in the refractive index of the eye. After a test period of time, the mounted cornea is then examined to determine whether any corneal collagen reorganization has occurred, and if so the extent of such reorganization. Toxicity resulting from the injection is also determined.

The examination of the cornea can be performed, for example, through slit-lamp examination to determine the clarity of the cornea; pachymetry to measure the thickness of the cornea; measurement of the tensile strength of the cornea; measurement of the distensibility of the cornea; and keratometry to measure central corneal curvature. The values determined from these tests are compared to values determined prior to the administration of the agent or enzyme.

In addition, a treated cornea in a mounted globe can be subjected to a number of other tests to determine the strength and viability of the cornea following treatment. For example, light microscopy, scanning, x-ray diffraction analysis, and transmission electron microscopy can be used to examine the morphology of the cornea; tissue culture is prepared to determine the viability of the cells of the cornea following treatment; biochemical studies can be made of the collagens and other structural components of the cornea following treatment.

The foregoing tests of donated globes and corneas can be used to verify that use of a particular enzyme or agent increases the transparency of the cornea, and yet does not decrease the viability of the corneal cells or damage the structural integrity of the cornea. Testing the use of an enzyme or agent on the cornea of a test animal, however, is also desirable in order to make sure that the candidate has no unexpected effect in living mammals that is not discovered during tests of donated eyes. In order to test the effect of a particular test enzyme or agent, a test dose in a pharmacologically acceptable carrier solution is administered to a test animal, in this case a mammal, so as to deliver that agent to the cornea of the animal.

Following the administration of an agent to the cornea of the animal, the animal's cornea can be subjected to the following examinations: slit lap examination to determine the clarity of the cornea, anterior chamber and iris; pachymetry to measure corneal thickness; computer assisted corneal topography to evaluate the surface topographical change of the cornea; measurement of the elasticity of the cornea; tonometry to measure intraocular pressure; fundoscopic examination in order to evaluate the optic nerve and retina; keratometry to measure central corneal curvature; retinoscopy to measure refractive error; staining with fluorescein or Rose Bengal to identify damage to the corneal epithelium; and indirect ophthalmoscopy. The values determined through these tests can be compared to values determined prior to the administration of the enzyme or agent, as well as to values determined for the untreated eye of the animal.

In addition, a treated cornea of a test animal can be subjected to a number of other tests to determine the clarity, strength, and viability of the cornea following treatment. For example, light microscopy, scanning, and transmission electron microscopy can be used to examine the morphology of the cornea; a tissue culture is prepared to determine the viability of the cells of the cornea following treatment; and biochemical studies can be made of the collagens and other structural components of the cornea following treatment.

Other corneal collagen-modifying enzymes and agents not disclosed herein and proper doses of such known and unknown enzymes and agents can be determined as described hereinabove in relation to determining enzymes and doses of enzymes.

Methods of Administration

Applicant has devised a method for a non-surgical clearance of corneal scars and corneal opacities. These methods generally comprise contacting the cornea with a corneal collagen reorganizing amount of an agent or enzyme in an amount which is effective to accelerate the clearance of corneal opacities. The corneal opacity clearing methods of the disclosed invention may be performed without any other surgical manipulation or removal of the cornea, thereby avoiding the potential risks and complications associated with penetrating keratoplasty.

The foregoing enzymes and agents for reorganizing the collagen of a subject's cornea may be administered in any way known to the art. For example, in one embodiment, an enzyme or agent is injected directly into the eye in a location proximal to the cornea. In this embodiment, the enzyme or agent should be mixed in a pharmacologically acceptable carrier that will not alter the effectiveness of the enzyme or agent contained therein.

In one particular embodiment of the disclosed invention, the route of administration of a corneal collagen reorganizing enzyme or agent is by intra-stromal injection. In this embodiment, an injectable solution containing one or more of the above-listed corneal collagen reorganizing enzymes or agents is injected, through a needle, directly into the stroma located within the anterior part of the eye.

In another embodiment of the disclosed invention, corneal collagen reorganizing enzymes and agents are administered to the eye of a subject by topical application in the form of eye drops. A sufficient number of drops are applied so as to administer a desired concentration of enzyme or agent to the cornea of the subject. The eye drop method of administration may be superior to injection based administration based on the less discomfort to the cornea of the subject resulting from an injection technique.

In still another embodiment, alternative means of aiding diffusion across the eye into the cornea may be used. Such means include, for example, the use of liposomes to deliver the active enzyme or agent. The enzyme or agent is packaged into liposomes, which can pass across the lipid soluble membrane of the corneal epithelium and into the corneal stroma. Other means of aiding diffusion include the use of an electrical current to make the outer membrane of the eye more permeable to the passage of enzymes and agents, known as iontophoresis.

In another embodiment, iontophoresis is used to administer the corneal collagen reorganizing reagents. Using this procedure, an electrical current traveling through a salt solution causes the agents to pass into the eye as charged particles.

In yet another embodiment of the disclosed invention, corneal collagen reorganizing enzymes and agents are administered to the cornea through use of a contact lens. As an example of one embodiment of the disclosed invention, a corneal collagen reorganizing amount of a corneal collagen reorganizing agent is loaded into a chamber inside a rigid contact lens, preferably one which is gas permeable. Alternatively, the enzyme or agent can be loaded or impregnated into a soft lens capable of taking up the enzyme or agent by soaking the soft lens in a solution containing the enzyme or agent. The enzyme or agent can also be loaded into a combination of a soft and a rigid lens.

In all of the following embodiments of a contact lens for administering a corneal collagen reorganizing enzyme or agent, the enzyme or agent is administered as it diffuses out of (is released from) the chamber in the lens or the material of the lens (if the enzyme or agent is soaked into a soft lens). Dosages for different contact lens delivery vehicles can be optimized through routine experimentation by one of skill in the art.

In accordance with one method of administration through contact lenses of the disclosed invention, corneal collagen reorganizing enzymes and agents can be applied to the eye through the use of rigid contact lenses. These lenses can be made from known fluoro silicone acrylate lens materials, which are gas permeable. The lens is provided with an internal chamber for storing the corneal collagen reorganizing enzyme or agent. The chamber preferably comprises a radially symmetrical space encircling the entire lens between the anterior surface and posterior surface of the lens.

Rigid lenses for the present purpose can conveniently be made by lathe cutting, molding, or milling a posterior component and an anterior component from a contact lens button which, during fabrication, can be secured together to form a unitary lens using bonding techniques or adhesives known in the art. The chamber can be formed by lathe cutting an annular recess into the convex surface of the posterior component of the lens before the final lens fabrication. Any of a variety of dimensions can be used in accordance with the disclosed invention, a preferred lens is provided with an annular chamber having a width of approximately 1.0 mm to about 1.5 mm and a depth of from about 0.05 mm to about 0.10 mm.

A plurality of microscopic holes are provided in the posterior portion of the lens to allow fluid communication between the chamber and the eye, thereby facilitating the timed release of the corneal collagen reorganizing enzyme or agent into the cornea. These holes may be provided by mechanical or laser drilling, or by molding prior to assembling the anterior component and posterior component of the lens. In one embodiment the holes are drilled using a mechanical drill having a microcarbon drill bit.

The pumping action of the eyelids combined with natural tearing assists the release of the corneal collagen reorganizing enzyme or agent through the tiny holes. Preferably, the holes are produced by mechanical drilling with a microcarbon bit and will have a diameter of from about 0.002 mm to about 0.010 mm, and preferably about 0.005 mm. The number and diameter of the holes can be varied to affect the time release characteristics, as will be apparent to one of skill in the art. In general, however, for the diameter ranges specified above, from about 3 to about 10 holes are contemplated to be used.

In one embodiment of the lens, the posterior portion of the lens has a centerpoint thickness of approximately 0.12 mm and an annular recess is lathed to a depth of about 0.075 mm. A number of holes, each having a diameter of about 0.005 mm, are drilled through the bottom of the chamber and spaced equidistantly apart around the periphery of the chamber to provide communication with the posterior surface of the lens. The number of holes in a lens will vary, depending on the desired rate of administration of corneal collagen reorganizing enzyme or agent from the chamber.

The anterior portion of the lens, having a centerpoint thickness of about 0.12 mm is thereafter secured to the posterior portion to enclose the annular recess and form a chamber, thereby forming a lens having an overall center thickness of about 0.24 mm. Bonding can be accomplished by applying a small amount of a bonding agent such as Concise™ enamel bonding system sold by 3M (St. Paul, Minn.). Other means of joining the posterior and anterior portions of the contact lens will be apparent to those of skill in the art.

In another aspect of the disclosed invention, a contact lens is provided which is composed of two layers which are laminated together. In this advantageous design for a contact lens of the disclosed invention, larger chambers for storing corneal collagen reorganizing enzyme or agent can be created.

In this contact lens, an anterior portion of the contact lens may be manufactured having an anterior surface and a posterior surface. A posterior portion of the contact lens may also be manufactured with an anterior surface and a posterior surface. The outer perimeter of the posterior surface of the anterior portion may be designed to have the same radius of curvature as the outer perimeter of the anterior surface of the posterior portion. In this way, when the posterior surface of the anterior portion and the anterior surface of the posterior portion are laminated together, a seal may be formed between the outer perimeters of the anterior and posterior portions.

However, in a central portion of the anterior portion, the posterior surface may have a steeper radius of curvature than the anterior surface of a central portion of the posterior portion. Because of this steeper radius of curvature, when the anterior portion and the posterior portion are laminated together, a chamber is formed between the central portion of the anterior portion and central portion of the posterior portion of the contact lens. The volume of the chamber can be adjusted by changing the radii of curvature of the posterior surface of the central portion and of the anterior surface of the central portion, as will be apparent to one of skill in the art.

Prior to manufacture, one or more holes may be made in the central portion of the posterior portion of the contact lens of this design. The holes may be produced by mechanical drilling with a microcarbon bit or by means of a laser such as an argon laser, and will have a diameter of from about 0.002 mm to about 0.010 mm, and preferably about 0.005 mm. The number and diameter of the holes can be varied to affect the time release characteristics, as will be apparent to one of skill in the art. Thus, the rate at which a dose of a corneal collagen reorganizing enzyme or agent is dispensed from the chamber is largely controlled by the size and number of holes present in the central portion of the posterior portion of the lens. In general, however, for the diameter ranges specified above, from about 3 to about 10 holes are contemplated to be used. These holes may be spaced around the central portion of the posterior portion of the contact lens in order to provide communication between the chamber and the surface of the eye of a subject wearing the lens.

In a preferred embodiment of this lens, the posterior portion of the lens may have a centerpoint thickness of approximately 0.125 mm. The anterior portion of the lens may have a centerpoint thickness of about 0.125 mm. When the anterior portion and the posterior portion are joined, a lens is created having an overall center thickness of about 0.24 mm. Bonding can be accomplished by applying a sufficient amount of a bonding agent such as the Concise™ enamel bonding system sold by 3M (St. Paul, Minn.). Other methods of bonding will also be apparent to one of skill in the art.

A lens of this embodiment of the disclosed invention may be made from known fluoro silicone acrylate lens materials. Such rigid lenses can be made by lathe cutting, molding, or milling a posterior component and an anterior component from a contact lens button. After the anterior and posterior components are manufactured, they can be secured together to form a unitary lens using bonding techniques, adhesives, or any other method of attachment known to the art. For example, an enamel bond system can be used to join the anterior and posterior contact lens portions. An example of such a system is the Concise™ enamel bond system sold by 3M (St. Paul, Minn.).

In an alternate embodiment of a contact lens of this aspect of the disclosed invention, a lens is provided which has a peripheral chamber rather than a chamber in the central portion of the lens. In this embodiment, the lens may be composed of an anterior portion and a posterior portion which are laminated together. In this embodiment, a chamber is provided in an intermediate portion of the lens.

In another embodiment, the chamber may be formed in the intermediate portion of the lens by providing an area of the posterior surface of the anterior portion of the lens, which has a steeper radius of curvature than that found in the remainder of the posterior surface of the anterior portion of the lens. As in the foregoing embodiment of a chambered contact lens, the volume of corneal collagen reorganizing enzyme or agent which can be contained in the lens and thus administered to a subject is largely determined by the radius of curvature of the posterior surface of the interior portion of the lens in the intermediate portion of the lens, as well as by the radius of curvature of the anterior surface of the posterior portion of the lens in the intermediate portion of the lens.

The posterior portion of the lens is also provided with holes through the posterior portion of the lens in the intermediate portion of the lens. These holes serve to allow the transfer of the contents of the chamber from the chamber to the eye of the subject. The number and size of the holes will largely determine the rate at which a corneal collagen reorganizing enzyme or agent is delivered to the eye.

Although the embodiments of a chambered contact lens have been described as being produced by laminating together an anterior portion and a posterior portion of the lens, one of skill in the art will recognize that other methods of forming the previously described chambers are also possible.

In accordance with a further delivery method of the disclosed invention, a soft lens bandage or shield may be soaked or charged with a dose of the corneal collagen reorganizing enzyme or agent. The soft lens may then be properly fit to the cornea and worn for a matter of hours to release the enzyme or agent into the cornea. After the enzyme or agent sufficiently modifies the collagen of the cornea, the soft lens either dissolves or is taken off.

Other types of soft lens materials tend to uptake less of a solution containing an enzyme or agent and also to release it more quickly. Examples of such materials are common hydrophilic soft lens materials such as etafilcon A and phemfilcon A, available from Vistacon and Wesley Jessen. These lenses can be the disposable or long-term wear variety. Lens having an $H_2O$ content of between about 58% and about 70% may be found to be useful in the disclosed method.

Fields of Use

One contemplated use of the disclosed invention is to treat corneal opacifications. Corneal opacifications may arise with age, as the corneal collagen loses its organization, or as a result of some trauma. The compositions and methods of the disclosed invention are useful in eliminating such corneal opacifications.

Another contemplated use of the disclosed invention is to rehabilitate irregularities and improve refractive errors that result from various corneal surgeries. The surgeries contemplated include photorefractive keratectomy (PRK), LASIK, radial keratotomy (RK), corneal transplant surgery, and cataract surgery. For example, LASIK is becoming an extremely common procedure worldwide. Although the technique itself is very successful, the incidents of side-effects from the treatment that are attributable to corneal collagen disorganization are growing. The disclosed invention can be used to improve visual acuity of a subject following the surgical reshaping of the cornea using various surgical techniques.

In this embodiment of the invention, a patient who had undergone the LASIK procedure would be identified and an acceptable corneal collagen reorganizing agent would be selected. Administration of the corneal collagen reorganizing agent may occur before, during or after the surgical procedure. In one embodiment, the subject could receive the corneal collagen reorganizing agent after the surgical procedure to facilitate proper healing of the cornea. As discussed above, routes of administration contemplated include injection and topical administration.

Similarly, the disclosed invention may also improve the chances of success for other corneal procedures, such as corneal transplant surgery and cataract surgery. One of the most common reasons for the clinical failure of surgical procedures like corneal transplants, is the existence of residual refractive errors following an otherwise successful surgery. The compositions and methods disclosed here can be used to correct the refractive error that occurs as a result of disease, surgery, or other conditions. Also, the compositions and methods of the disclosed invention, by improving the visual acuity resulting from a surgical procedure, will reduce or eliminate the need for subsequent surgeries that are now required to eliminate unwanted refractive errors.

To use the foregoing methods of the disclosed invention to effect these further clinical benefits, subjects who have corneal opacification, corneal collagen disorganization, or who have under gone a corneal manipulation are first identified. Such identification is normally accomplished by an eye specialist or other practitioner skilled in the art who can diagnose an individual as having corneal opacification, corneal collagen disorganization, or having undergone corneal manipulation. The previously described methods of administration are then used to induce corneal collagen reorganization to produce enhanced visual acuity.

EXAMPLES

Example I

Ophthalmic Toxicities of Thimerosal Hyaluronidase (ACS) and Hyaluronidase (Wydase®) in Rabbits Fifty-two (52) healthy rabbits of the New Zealand Cross variety (26 male, 26 female) weighing 1.5 kg to 2.5 kg were individually marked for identification and were housed individually in suspended cages. The animals received a commercially available pelleted rabbit feed on a daily basis, with tap water available ad libitum.

The animals were divided into thirteen groups of 4 animals each (2 males, 2 femals). Two animals in each group (1 male, 1 female) were selected for pretreatment fundus photography and fluorescein angiography.

The fundus photography was performed by restraining the animals and visualizing the optic nerve, retinal arcades and fundus with a KOWA® RC-3 Fundus Camera loaded with Kodak Gold 200 ASA film.

The fluorescein angiography involved a 1.5-ml injection of 2% sterile fluorescein solution via the marginal ear vein. Approximately 30 seconds post-injection the fluorescein was visualized upon localization of the optic nerve, retinal vessels and fundus.

The following day, each animal was anesthetized by intravenous administration of a combination of 34 mg/kg of ketamine hydrochloride and 5-mg/kg xylazine. The eyelids were retracted using a lid speculum, and the eyes were disinfected with an iodine-povidone wash.

Experimental treatments of either balance salt solution (BSS), BSS+thimerosal, (Wydase®) or hyaluronidase (ACS) were administered by injection using a 1 cc tuberculin syringe with a 30 gauge, 0.5 inch needle attached thereto. The hyaluronidase (ACS) solution utilized in this example was free of thimerosal and constituted the specific preferred hyaluronidase (ACS) formulation set forth in Table II hereabove. The experimental treatments administered to each animal group were as follows:

TABLE VI

| Group # | Treatment |
| --- | --- |
| 1 | BSS |
| 2 | BSS + 0.0075 mg Thimerosal |
| 3 | BSS + 0.0025 mg Thimerosal |
| 4 | Hyaluronidase (Wydase) 1 IU |
| 5 | Hyaluronidase (Wydase) 15 IU |
| 6 | Hyaluronidase (Wydase) 30 IU |
| 7 | Hyaluronidase (Wydase) 50 IU |
| 8 | Hyaluronidase (Wydase) 150 IU |
| 9 | Hyaluronidase (ACS) 1 IU |
| 10 | Hyaluronidase (ACS) 15 IU |
| 11 | Hyaluronidase (ACS) 30 IU |
| 12 | Hyaluronidase (ACS) 50 IU |
| 13 | Hyaluronidase (ACS) 150 IU |

The day following the injections (Day 1) the 26 animals, which were subjected to the fundus photography and fluorescein angiography, were observed using the same methods as for the pre-dose examination.

On Day 2 following the injections, the 13 male rabbits that had received the fundus photography and fluorescein angiography at pre-dose and Day 1, as well as the 13 female rabbits that were not selected for photography were euthanized with a sodium pentobarbital based drug. The eyes were then surgically removed and placed in a fixture solution of 2.5% glutaraldehyde with 0.1M phosphate buffered saline at pH 7.37. Alternatively, one randomly selected rabbit was euthanized by pentobarbital injection but then fixed by intracardiac injection of the gluteraldehyde solution into the left ventricle to determine the effect of the fixation procedure on the histology findings within the enucleated eyes.

On Day 7, the 13 female rabbits that had been previously photographed and angiography performed were subjected to same observations following the methods previously described.

The remaining 26 animals were euthanized as described above 7 days after dosing. The eyes were fixed in the same manner as those, which had been fixed on day 2. Also, one randomly selected rabbit was subjected to the same intracardiac gluteraldehyde fixation procedure described hereabove for the previously randomly selected animal.

The eyes of the animals treated in this example were examined grossly and microscopically for evidence of treatment-related toxicities. A table setting forth a summary of the histological evidence of toxicity or non-toxicity in each treatment group, is set forth in Table VII below.

In summary, the eyes of the BSS-treated control group were free of toxicity at 2 and 7 days post dose.

The eyes of the Group No. 2 animals treated with BSS+ thimerosal (0.0075 mg) were free of toxicity at day 2, but exhibited evidence that there was a breakdown of the blood retinal barrier at day 7.

The Group No. 3 animals treated with BSS+thimerosal (0.025 mg) exhibited severe treatment-related toxic effects, at day 2 and 7 post dose.

The Group No. 4 animals treated with Wydase® at the 1 IU dose were free of toxicity at days 2 and 7, however, the eyes of the animals in Group Nos. 5–8 treated with Wydase® at dosages ranging from 15 IU–150 IU exhibited generally dose-related toxic effects at days 2 and 7 post dose.

The eyes of animals in treatment Groups Nos. 9–13 treated with hyaluronidase (ACS) at dosages ranging from 1 IU through 150 IU, were free of evidence of toxic effects at days 2 and 7 post dose.

Accordingly, it is concluded that thimerosal and the thimerosal-containing Wydase® formulation do cause toxic effects in the eyes of rabbits at the dosages tested, however, hyaluronidase (ACS) caused no toxic effects in these animals at the dosages tested.

The results of the examinations conducted on day 7 are summarized in Table VII. As shown in Table VII, significant toxic effects were observed on day 7 in the eyes of rabbits treated with BSS plus thimerosal (0.0075 mg) and hyaluronidase (Wydase®) at all doses between 1 IU–150 IU. In contrast, no toxic effects were observed in the eyes of animals treated with hyaluronidase (ACS) at doses between 1–150 IU.

TABLE VII

Toxic Effects of Single Dose Intravitreal Injection of BSS, BSS + Thimerisol, Hyaluronidase (ACS) and Hyaluronidase (Wydase ®) in Rabbits

| | | Results At Day 7 | |
| --- | --- | --- | --- |
| Group | Treatment & Dosage (Volume = 100 :L) | Fundus Photography & Fluorescein Angiography | Histology |
| 1 | BSS | Normal | Normal |
| 2 | BSS + Thimerisol (0.0075 MG) | Breakdown of blood-retinal barrier. | Retinal necrosis. |
| 3 | BSS + (0.025 mg) | Severe retinal effects & intravitreal hemorrhage. | Severe retinal necrosis. |
| 4 | Hyaluronidase (Wydase) –1 IU | Slight fluorescein leakage. Compromised blood-retinal barrier. | No significant change. |
| 5 | Hyaluronidase (Wydase) –15 IU | Severe retinal damage. | Equivocal changes. |
| 6 | Hyaluronidase (Wydase) –30 IU | Severe retinal damage. | Retinal necrosis. |

TABLE VII-continued

Toxic Effects of Single Dose Intravitreal Injection of BSS, BSS + Thimerisol, Hyaluronidase (ACS) and Hyaluronidase (Wydase ®) in Rabbits

|  |  | Results At Day 7 |  |
|---|---|---|---|
| Group | Treatment & Dosage (Volume = 100 :L) | Fundus Photography & Fluorescein Angiography | Histology |
| 7 | Hyaluronidase (Wydase) –50 IU | Extensive retinal damage and retinal detachment. | Retinal necrosis. |
| 8 | Hyaluronidase (Wydase) –150 IU | Extensive retinal damage and retinal detachment | Severe retinal necrosis. |
| 9 | Hyaluronidase (ACS) –1 IU | Normal | Normal |
| 10 | Hyaluronidase (ACS) –15 IU | Normal | Normal |
| 11 | Hyaluronidase (ACS) –30 IU | Normal | Normal |
| 12 | Hyaluronidase (ACS) –50 IU | Normal | Normal |
| 13 | Hyaluronidase (ACS) –150 IU | Compromised blood-retinal barrier | Normal |

Example II

Ophthalmic Toxicities of Thimerosal, Hyaluronidase and Hyaluronidase (Wydase®) Injected in Rabbit Corneas Twenty (20) healthy rabbits of the New Zealand cross variety weighing 1.5 kg to 2.5 kg, were individually marked for identification and were hosed individually in suspended cages. The animals received a commercially available pelleted rabbit feed on a daily basis, with tap water available ad libitum.

The animals were divided into 4 groups of 5 animals each. All 20 animals were examined pre-treatment by slit lamp biomicroscopy and fluorescein staining for pre-treatment health of the rabbit corneas.

The following day, each animal was anesthetised by intravenous administration of a combination of 34 mg/kg of ketamine hydrochloride and 5-mg/kg xylazine. The eyelids were retracted using a lid speculum, and the eyes were disinfected with an iodine-povidone wash.

Experimental treatments of either balanced salt solution; Hyaluronidase (Wydase®) or Hyaluronidase (ACS) was administered by injection using a 0.3 cc tuberculin syringe with a 29 gauge, 0.5-inch needle attached thereto. The hyaluronidase (ACS) solution utilized in this example was free of thimerosal and constituted the specific preferred hyaluronidase ACS formulation set forth above.

The experimental treatments administered to each animal group were as follows:

| GROUP NO. | TREATMENT | |
|---|---|---|
|  | Right Eye | Left Eye |
| 1 | BSS | Untreated control |
| 2 | Hyaluronidase (Wydase) 25 IU | Hyaluronidase (Wydase) 100 IU |

-continued

| GROUP NO. | TREATMENT | |
|---|---|---|
|  | Right Eye | Left Eye |
| 3 | Hyaluronidase (ACS) 25 IU | Hyaluronidase (ACS) 100 IU |
| 4 | Hyaluronidase (ACS) 500 IU | Hyaluronidase (ACS) 1000 IU |

On days 1, 7, 15, and 30 following the injections, the eyes of the animals were examined grossly and biomicroscopically for evidence of treatment related toxicities.

In summary, the eyes of the BSS treated and untreated control groups were free of toxicity.

The eyes of Group 2 animals treated with Hyaluronidase (Wydase®) preserved with thimerosal were found to be toxic. The eyes of Group 3 and Group 4 animals treated with hyaluronidase (ACS) were found to be free of toxicity.

Accordingly, it is concluded that thimerosal containing Wydase® formulation does cause toxic effects in the eyes of rabbits at the dosages tested. However, hyaluronidase (ACS) caused no toxic effects for these animals at the dosages tested.

Example III

Corneal Opacity Clearing Efficacy of Hyaluronidase in Human Donor Corneas

Human donor corneas with stromal scars were obtained within 24–48 hours after death. The corneas were photographed to document the position of the scar. The corneas were then placed in org,an culture for 72 hours. The culture medium consisted of serum-free modified Dulbeccos MEM supplemented with chondroitin sulfate, EGF, dextran, selenium and Vitamin A. Corneas were cultured in a 10 mm sterile culture dish containing 10 to 12 mls of the culture medium, epithelial side up. The dish was then placed on a rocker platform in a humidified incubator at 37° C. and in a 5% CO2 environment and rocked so that the epithelial surface of the tissue was intermittently exposed to an air:liquid interface.

At day 3, test corneas received intrastromal injections of Hyaluronidase (ACS) reconstituted in sterile saline (500 IU/20 μl) adjacent to the scar, with the bevel of the injecting needle pointing towards mid-cornea. The control group of corneas were injected with saline at day 3. All corneas were then returned to culture. The test corneas were subsequently injected with Hyaluronidase (ACS) (500 IU/20 μl) on day 7 as described above.

The corneas were examined daily for scar resolution. Resolution was determined by the presence or the absence of the corneal opacity. At the conclusion of the experiment the corneas were re-photographed and then processed for light and electron microscopy.

Results

Corneas retained good morphology with minimal swelling in culture. The corneas were cultured for 72 hours before injection of Hyaluronidase (ACS) to ensure that the culture system itself did not influence the scar morphology. The results of this experiment are summarized in the table below. No changes in scar appearance were observed during this period. Immediately after Hyaluronidase (ACS) injection into the corneal stroma, an area of localized haze develops at the site of injection. The haze is thought to be due to the injection of fluid into the stroma, and typically resolved itself within 4–8 hours after injection. To date, a total of 14 scarred human corneas have been studied and in 12 out of 14 cases, within 2–4 days after Hyaluronidase (ACS) treatment the scars were no longer visible by examination with the naked eye. The scars varied in type and location from peripheral post-surgical scarring as seen commonly after IOL insertion to scars resulting from accidental trauma. Most of the scars we examined were of an unknown origin.

Intrastromal injection of Hyaluronidase (ACS) appears to be very effective for effecting resolution of corneal opacities as an alternative treatment to corneal transplantation.

The corneas were then dissected and fixed in 1% gluteraldehyde solution, processed and embedded in plastic, or placed in organ culture. The corneas that were placed in culture were grouped as follows: a) untreated controls; b) saline injected controls; and c) Hyaluronidase injected (50 IU/20 µl) treatment group. The corneas were cultured, epithelial side up, in a 10 mm sterile culture dish containing 10 to 12 mls of culture medium. The culture medium consisted of serum-free modified Dulbeccos MEM supplemented with chondroitin sulfate, EGF, dextran, selenium and Vitamin A. The dish was then placed on a rocker platform in a humidified incubator at 37° C. and in a 5% $CO_2$

| | PATIENT DATA | | | | SCAR APPEARANCE | |
|---|---|---|---|---|---|---|
| Expt # | Age | Sex | OD/OS | HRS post Mortem | Pre-hyaluronidase Treatment | Post H'ase |
| RL 7-16 | 56 | M | OS | 20 HRS | Crescent-shaped scar, origin unknown ~4 mm extending from the corneal-scleral junction to arc mid cornea | Scar not visible to naked eye by 72 hours |
| RL 7-31 | 80 | F | OD | 22 HRS | Suture scars, origin from cataract surgery, 3 circular scars adjacent to corneal-scleral junction | Scar not visible to naked eye by 96 hours |
| RL 7-31 | 80 | F | OS | 22 HRS | Irregular long (3 mm) & wide (2 mm) scar, possible origin from cataract surgery | Scar not visible to naked eye by 96 hours |
| RL 8-03 | 33 | M | OD | 28 HRS | Linear scar, origin unknown, 1 mm in length, extending from the arcus into the corneal stroma | Scar not visible to naked eye by 48 hours |
| RL 8-04 | 54 | M | OS | 36 HRS | Linear scar, trauma, 1–1.5 mm in length, extending from the arcus into the corneal stroma | Scar not visible to naked eye by 48 hours |
| RL 8-24 | 66 | M | OD | 36 HRS | Small circular corneal opacity, <1 mm in radius, located off central cornea | Scar not visible to naked eye by 72 hours |
| RL 8-24 | 57 | M | OD | 36 HRS | Linear scar, origin unknown, <1 mm in length, extending from the arcus into the corneal stroma | Scar not visible to naked eye by 72 hours |
| RL 9-02 | 80 | F | OD | 40 HRS | Irregular corneal opacity, approx. 1–2 mm in width, located adjacent to mid-cornea | Scar not visible to naked eye by 120 hours |
| RL 9-03 | 30 | F | OD | 36 HRS | Linear scar, 2–3 mm in length, arcing adjacent to the corneal-scleral junction, possibly of surgical origin | Scar not visible to naked eye by 72 hours |
| RL 9-08 | 72 | M | OS | 25 HRS | Multiple small linear scars adjacent to the corneal-scleral junction | Scar did not resolve |
| RL 10-06 | 76 | M | OD | 96 HRS | Small surgical scar adjacent and parallel to sclera, possibly surgical. Eye was pseudophakic | Scar not visible to naked eye by 96 hours |
| RL 10-06 | 76 | M | OS | 108 HRS | Large diffuse opacity adjacent to sclera, approx 2 mm width and 2 mm length. Eye was pseudophakic. | Scar did not resolve |
| CB-COt-11-16 | 54 | M | OD | 96 HRS | Linear scar, 3 mm in length arcing from corneal-scleral junction to approx mid-cornea | Scar resolved by 144 hours |
| CB-COt-11-16 | 54 | M | OS | 96 HRS | Small linear scar 1 mm below mid cornea | Scar resolved by 144 hours |

Example IV
Effect of Hyaluronidase on the Ultrastructure of Human Donor Corneas

Human donor corneas were obtained within 24–48 hours after death of the donor for use in the following example.

environment and rocked so the epithelial surface of the tissue was intermittently exposed to an air:liquid interface.

At the end of the treatment period the corneas were dissected and fixed in 1% gluteraldehyde solution, processed and embedded in plastic. Full transverse sections (1 µm) from the mid-stromal regions were stained and examined by light microscopy. In addition ultrathin sections (0.1 µm) were subsequently cut and examined by transmission electron microscopy. The ultrastructural changes in the collagen fibril density was determined from the electron micrographs (124,000× magnification) by counting the average number of collagen fibrils per 180 square mm. The results of this study are summarized in Table VIII.

TABLE VIII

Collagen Fibril density Counts from Electron Micrographs. (124,000× Magnification)

| Age/Sex | Treatment | Sample Size | Ave. # Fibers/ 180 sq. mm. | % Difference from Normal | P (T <= t) Two tail |
|---------|-----------|-------------|----------------------------|--------------------------|---------------------|
| 65/M | Normal Tissue | N = 20 | 47.5 | 0.00% | — |
| 80/F | 48 Hours @ hyaluronidase | N = 10 | 56.4 | 18.62% | 0.00592 |
| 80/M | 48 Hours @ Saline | N = 4 | 52.7 | 10.97% | 0.56211 |

Results

The results show a 18.62% increase in the reorganization of the collagen fibers 48 hours after the injection of hyaluronidase enzyme. This magnitude of collagen fiber compaction and reorganization for the 80 year old female cornea is very significant statistically from the untreated 65 year old male cornea. Intrastromal injection of Hyaluronidase (ACS) was very effective for effecting corneal collagen fiber reorganization.

Example V

Corneal Opacity Clearing Efficacy of Hyaluronidase in Humans

In this study, two (2) human patients who presented with corneal opacities were treated with a single intrastromal injection of Hyaluronidase at a dose level of 500 IU for Patient #1 and 800 IU for Patient #2. The observed results of this experiment are summarized in Table IX.

TABLE IX

| Patient# | Dose of Hyaluronidase Injected | Corneal Opacity Pre-treatment | Corneal Opacity 1-Week Post-Treat. | Corneal Opacity 1-Month Post-Treat. | Corneal Opacity 6 Months Post-Treat. |
|---|---|---|---|---|---|
| Female Patient | 500 IU | Heavy Corneal Opacity | Corneal Haze +1 | Clear Cornea | Clear Cornea |
| Male | 800 IU | Corneal Scar | Anterior Stromal Opacity | Clear Cornea | *Clear Cornea |

*2 months post-treatment

In the two (2) patients treated in this example, the corneal opacity became sufficiently clear within 30 days of the single intrastromal injection of the hyaluronidase (ACS). Such clearing of the cornea would not have occurred in these patients without hyaluronidase treatment.

Example VI

Use of Hyaluronidase to Resolve a Corneal Scar

A patient presenting a corneal scar is identified as requiring corneal collagen reorganization to improve her visual acuity. The subject is treated with an intra-stromal injection of hyaluronidase ACS as disclosed in Table IV. The pharmacological composition is injected into the stroma of the eye containing the corneal scar.

The hyaluronidase ACS treatment of the disclosed invention is commenced after a full ophthalmic examination to establish a baseline of ocular health has been performed. The ophthalmic examination includes: indirect ophthalmoscopy, slit-lamp biomicroscopy, peripheral retinal examination, intraocular pressure measurements, visual acuity (unaided and best corrected), and symptomatology.

Following the preliminary examination, an intra-stromal injection of hyaluronidase ACS is given to the patient's affected eye. If both eyes are affected, they may be treated separately. The eye to be treated is injected with 40:1 of a composition containing 50 IU of the hyaluronidase ACS ophthalmic solution described above intra-stromally to promote the reorganization of the corneal collagen fibers and resulting in the elimination of the corneal scar over time.

After treatment, the patients' eyes are to be examined on days one (1), two (2), seven (7), fifteen (15), thirty (30) and sixty (60). On each examination day the patient is monitored for corneal scar clearance. At the conclusion of the treatment period, the corneal scar is eliminated.

Example VII

Use of Hyaluronidase to Resolve Corneal Opacification

A subject presenting a corneal opacification is identified as requiring corneal collagen reorganization to improve her visual acuity. A corneal collagen reorganizing pharmaceutical composition is administered topically to the eye containing the corneal opacification via a soft contact lens pre-treated with the composition disclosed in Table IV. The corneal opacification is resolved as a result of the treatment.

Example VIII

Use of Hyaluronidase to Improve Visual Acuity Following Radial Keratotomy (RK)

A subject who has undergone RK and is presenting signs of impaired vision, including glare or starbursts around lights (haze) is identified as requiring corneal collagen fiber reorganization. During the RK procedure the clinician makes a series of cuts (usually 4 to 8) in the cornea with a scalpel, in a pattern that resembles a wheel spokes. These cuts are fairly deep, sometimes to 90% of the thickness of the cornea. The cuts resemble the letter "V" and cause the central cornea to relax or flatten and the peripheral cornea to steepen. These alterations in the conformation of the cornea reduce the dome of the central cornea with a resulting improvement in uncorrected vision. After the incisions have been made, the edges of the cuts will merge and heal. During this healing process the collagen fibers will merge, however, the organization of the fibers in the incision area will not have the same level of organization as that found in the unaltered portion of the cornea. The lack of organization of the collagen fibers at these sites often results in corneal haze.

Approximately one week subsequent to the RK procedure, the subject is injected with the hyaluronidase containing solution disclosed in Table IV. The corneal collagen fibers in the incision areas made during the RK procedure are reorganized as a result of the hyaluronidase administration. As a result of the treatment, the corneal haze is resolved.

Example IX

Use of Hyaluronidase to Improve Visual Acuity During Radial Keratotomy (RK)

A subject who is undergoing RK as described generally in Example VIII is injected with the hyaluronidase containing solution disclosed in Table IV immediately following the incisions made in the cornea As a result of the administration of hyaluronidase, the corneal collagen fibers that will heal the incision areas made during the RK procedure will be more organized than fibers that have healed in an untreated eye. This adjunct procedure to RK serves to prevent corneal haze.

Example X

Use of Hyaluronidase to Improve Visual Acuity Following Photorefractive Keratotomy (PRK)

A subject who has undergone PRK and is presenting signs of impaired vision, including glare or starbursts around lights (haze) is identified as requiring corneal collagen fiber reorganization. Rather than making cuts in the cornea as is done with RK, the PRK process uses an excimer laser to sculpt an area 5 to 9 millimeters in diameter on the surface of the eye. This process removes only 5–10% of the thickness of the cornea for mild to moderate myopia and up to 30% for extreme myopia—about the thickness of 1 to 3 human hairs. The major benefit of this procedure is that the integrity and the strength of the corneal dome is retained. The excimer laser is set at a wavelength of 193 nm, which can remove a microscopic corneal cell layer without damaging any adjoining cells. This allows the clinician to make extremely accurate and specific modifications to the cornea with little trauma to the eye.

As the cornea recovers from the PRK procedure, corneal collagen fibers are repaired and rejoined. Corneal collagen fiber organization suffers during this healing process, resulting in the creation of corneal haze.

Approximately one week subsequent to the PRK procedure, the subject is injected with the hyaluronidase containing solution disclosed in Table IV. The corneal collagen fibers in the incision areas made during the PRK procedure are reorganized as a result of the hyaluronidase administration.

Example XI

Use of Hyaluronidase to Improve Visual Acuity During Photorefractive Keratotomy (PRK)

A subject who is undergoing PRK as described in Example X is administered a hyaluronidase containing solution disclosed in Table IV in drop form, immediately following laser treatment. The corneal collagen fibers in the incision areas made during the PRK procedure are reorganized as a result of the hyaluronidase administration. This adjunct procedure to RK serves to prevent corneal haze.

Example XII

Use of Hyaluronidase to Improve Visual Acuity Following LASIK

A subject who has undergone LASIK and is presenting signs of impaired vision, including glare or starbursts around lights (haze) is identified as requiring corneal collagen fiber reorganization. Using a microkeratome or other similar device, the clinician slices the cornea from the side, producing a flap. A part of the device flattens the cornea during the slice, so as to create a flap of uniform thickness. It is at this stage of the procedure that the clinician must exercise extreme precision and caution to create a perfect flap. Following creation of the flap, this tissue is folded back to expose the inner layers of the cornea.

With the flap folded back, the clinician now makes the refractive correction on the inner layer of the cornea—done with excimer laser similar to PRK. When treatment is complete, the flap is repositioned in its original position and the procedure is complete. The eye has a natural suction facility that keeps the flap firmly in place at this time. Care must be taken by the clinician to ensure an excellent fit when repositioning the flap. Because very little of the epithelium has been disturbed, patients report a high comfort level after the procedure. However, even when the flap is perfectly repositioned, corneal collagen fibers will be repaired causing a certain degree of disorganization at the perimeters of the flap.

Approximately one day subsequent to the LASIK procedure, the subject is injected with the hyaluronidase containing solution disclosed in Table IV. The corneal collagen fibers in the incision areas made during the LASIK procedure are reorganized as a result of the hyaluronidase administration. This adjunct procedure to RK serves to prevent corneal haze.

Example XIII

Use of Hyaluronidase to Improve Visual Acuity During LASIK

A subject who is undergoing LASIK is administered and is the hyaluronidase containing solution disclosed in Table IV in drop form immediately following the resurfacing of the cornea as described in Example XII. Following administration of the hyaluronidase containing solution, the flap is resorted and allowed to heal. After repositioning the flap, the corneal collagen fibers will be repaired and grow in a more organized manner as compared to LASIK treated corneal tissue not treated with a hyaluronidase containing solution. This adjunct procedure to RK serves to prevent corneal haze.

The foregoing detailed description and examples have described the disclosed invention with reference to certain embodiments. It will be appreciated by those skilled in the art that various deviations may be made from the specific embodiments and formulations described herein, without departing from the intended spirit and scope of the disclosed invention. Accordingly, it is intended that all such reasonable deviations be included within the scope of the following claims.

REFERENCES

The references cited herein are hereby incorporated by reference in their entirety.

1. Borcherding, M., Blacik, L., Sittg, A., Bizzell, J., Breen, M., and Weinstein, H. (1975). Proteoglycans and collagen fiber organization in human comeoscleral tissue. *Exp. Eye Res.* 21, 59–70.

2. Campbell, C., Koester, C., Rittler, M. C., Tackaberry, R. (1974), *Physiologic Optics, New York, NY: Harper & Row;* 199–206.

3. Cintron, C., and Kublin, C. (1977) *Dev. Biol.* 61, 346–357.

4. Cintron, C., Gregory, J. D., Dawle, P. S., and Kublin, L. C. (1990). *Invest. Ophthal. & Vis. Sci.* 31, 1975–1981.

5. Cintron, C., Hassinger, L. C., Kublin, C. L., and Cannon, D. J. (1978). *J. Uptrastract. Res.* 65, 13–22.

6. Fitzsimmons, T. D., Molander, N., Stenevi, U., Fagerholm, P., Schenholm, M., and Von Malmborg, A. (1994). *Invest. Ophthalmol. Vis. Sci.* 35, 2774–82.

7. Hassell, J. R., Cintron, C., Kublin, C. L., and Newsome, D. A. (1980). Proteoglycan changes during restoration of transparency in corneal scars. *Archives of Biochemistry and Biophysics.* 222 (2), 362–369.

8. Hassell, R. J., Newsom, A. D., Krachmer, J. H., and Rodriguez, M. M. (1983). *Proc. Nat'l. Acad. Sci.* 77, 3705–3709.

9. Howland, H. C., Howland, B. (1977). A subjective method for the measurement of monochromatic aberrations of the eye. *J. Opt. Soc. Am* 67: 1508–1518.

10. Kato, T., Nakayasu, K., Hosoda, Y., Watanobe, Y., Kanai, A. (1999) Corneal wound healing following laser insitu keratomileuis (LASIK): a histopathological study in rabbits. *J Ophthalmol* 83: 1302–1305.

11. Maurice, D. M. (1957). The structure and transparency of the cornea. Br. *J Physiol.* 136, 262–87.

12. Oshika, T., Klyce, S., Applegate R., Howland, H., Danasoury M. A. (1999). Comparison of corneal wavefront aberrations after photorefractive keratectomy and laser in situ keratomileusis, *Am. J. of Ophthalmolo.* 127: 1–7

13. Pallikaris, I. (1998) Quality of vision in refractive surgery. *J Refract Surg.* 14:551–558.

14. Schwarz, W., and Keyserlingk, D. G. (1969). In the cornea macromolecular organization of a connective tissue. John Hopkins Press, Baltimore/London. 123–132.

15. Toole, B., and Trelstad, R. (1971). Hyaluronate production and removal during corneal development in the chick. *Dev. Biol.* 26, 28–35.

16. Seiler T., Holschback, F., Derse, M., Genth, U. (1994). Complications of myopic photorefractive keratectomy with the eximer laser. *Ophthalmology.* 101:153–160.

17. Seiler, T., Reckmann, W., Malong, R. K. (1993) (↑) J. *Cataract Refract Surb.* 19 (Suppl): 155–165 (↑) Effective spherical aberration of the cornea as a quantitative descriptor in corneal topography.

18. Verdon, W., Bullimore, M., Maloney, R. K. (1996). Visual performance after photorefractive keratectomy: a prospective study. Arch Ophthalmol. 114: 1465–1472.

19. Vogel, K. G., and Trotler, J. A. (1987). The effects of proteoglycans on the morphology of collagen fibrils formed in vitro. *Collagen Relat. Res.* 7, 105–114.

What is claimed is:

1. A method for clearing corneal opacity comprising the step of administering a corneal scar, opacity, and haze clearing amount of an enzyme, whereby a corneal scar, opacity, and haze are eliminated.

2. The method of claim 1, wherein said enzyme is selected from the group consisting of glycoaminoglycanases, metalloproteases, and protein-kinases.

3. The method of claim 2, wherein said glycoaminoglycanase is selected from the group consisting of hyaluronidase, keratinase, chondroitinase AC, chondroitinase β, chondroitinase ABC, chondroitinase 4 sulfatase and combinations thereof.

4. The method of claim 2, wherein said glycoaminoglycanases is hyaluronidase.

5. The method of claim 4, wherein said hyaluronidase is administered at between 1 and 8000 International Units.

6. The method of claim 4, wherein said hyaluronidase is in purified form.

7. The method of claim 6, wherein said hyaluronidase is devoid of hyaluronidase MW fractions above 100,000, between 60,000–70,000, and below 40,000 using 10% SDS-PAGE.

8. The method of claim 2, wherein said metalloproteinase is selected from the group consisting of metalloproteinase 1, 2, 3, and 9.

9. The method of claim 2, wherein said protein-kinase enzyme is selected from the group consisting of streptokinase and urokinase.

10. The method of claim 1, wherein administration is performed by intrastromal injection.

11. The method of claim 1, wherein administration is performed by contact lens.

12. The method of claim 1, wherein administration is performed by topical application.

13. The method of claim 1, wherein said administration step is performed a single time.

14. The method of claim 1, wherein said administration step is performed at least twice.

15. The method of claim 1, wherein said corneal scar, opacification, and haze results from a surgical procedure selected from the group consisting of cataract surgery, corneal transplantation, RK, PRK, and LASIX.

* * * * *